US005352191A

United States Patent [19]

Sunago et al.

[11] Patent Number: 5,352,191

[45] Date of Patent: Oct. 4, 1994

[54] TRANSFUSION DEVICE

[75] Inventors: Seizo Sunago, Hyogo; Osamu Aoki, Osaka, both of Japan

[73] Assignee: Fujisawa Pharmaceutical Co., Ltd., Osaka, Japan

[21] Appl. No.: 960,838

[22] Filed: Oct. 14, 1992

[30] Foreign Application Priority Data

Oct. 25, 1991 [JP] Japan .................................. 3-279770

[51] Int. Cl.[5] .............................................. A61M 5/00

[52] U.S. Cl. .......................................... 604/7; 604/82; 604/88; 604/411

[58] Field of Search ....................... 604/7, 413, 82, 88, 604/403, 408, 411, 412, 414, 87, 91, 56, 89, 416, 86, 90; 206/222, 219; 141/329, 330

[56] References Cited

U.S. PATENT DOCUMENTS

D. 323,389 1/1992 Aoki et al. .
4,583,971 4/1986 Bocquet et al. .
4,781,679 11/1988 Larkin .
4,936,841 6/1990 Aoki et al. .

FOREIGN PATENT DOCUMENTS 0091310 10/1983 European Pat. Off. .
0335378 10/1989 European Pat. Off. .
0395758 11/1990 European Pat. Off. .

*Primary Examiner*—C. Fred Rosenbaum
*Assistant Examiner*—Vanitha Alexander
*Attorney, Agent, or Firm*—Oblon, Spivak, McClelland, Maier & Neustadt

[57] ABSTRACT

A transfusion device comprising a flexible vessel containing a solvent fluid, a plugged drug container containing a drug, and a communicating portion for communicating the vessel and the container with each other, the communicating portion comprising a communicating passage disposed at a top portion of the flexible vessel and having the drug container partially or wholly fitted therein, a plugged mouth portion of the container facing downward, a membrane disposed in the communicating passage for closing the passage, and a particular puncturing needle unit mounted in the communicating passage for enabling the vessel and container to communicate with each other. When the puncturing needle unit is pressed externally through the flexible vessel, the needle breaks the membrane and the plug member of the drug container to enable the vessel and container to communicate with each other.

5 Claims, 7 Drawing Sheets

TRANSFUSION DEVICE

BACKGROUND OF THE INVENTION

1. Field of the Invention

The present invention relates to a transfusion device, and more particularly to a transfusion device (container) used for drip infusion.

2. Description of the Prior Art

Hitherto, a drug in the form of powders or freeze-dried powders contained in a vessel such as a vial has been dissolved with a solvent and used as fluid for drip infusion at a medical organization such as a hospital. In that case, a vessel containing the drug is connected to a vessel containing a liquid for dissolving the drug by means of a connector such as a double-edged needle or communicating pipe.

The liquid for dissolving the drug is moved into the vessel containing the drug to dissolve the drug therewith.

Such procedure is, however, complicated and time consuming. Moreover, there is a possibility of the drug in the vessel being contaminated because a hole for connection is formed on the vessel containing the drug in the open air.

In order to solve the above mentioned problem, there has been proposed a transfusion device (container) as shown in Japanese Unexamined Patent. Publication No. 61-501129 (which corresponds to U.S. Pat. No. 4,583,971).

As shown in FIG. 11, the transfusion device comprises a capsule (102) enclosing a vial (101), i.e., a drug container, and a flexible vessel (103) containing a liquid for dissolving a drug and having a fluid outlet, the capsule and the flexible vessel being connected to each other through a tube (104). In the tube (104), a hollow needle (105) is provided on the vial (101) side while a breaking member (106) is provided on the flexible vessel (103) side. The breaking member (106) closes a passage of the tube (104) and obstructs a flow of fluid.

In use, a cap (107) on the top of the capsule (102) is pushed with a finger to press down the vial (101). The needle (105) penetrates a rubber plug (108) of the vial (101) so that the flexible vessel (103) and the vial (101) are connected to each other. The breaking member (106) in the tube (104) is then bent with hands to open the passage of the tube (104) and to mix the drug and the liquid for dissolving the drug.

The above mentioned transfusion device has been improved in the point that mixing procedure is performed by communicating a drug container to a flexible vessel containing a liquid for dissolving the drug. The mixing procedure is still troublesome because a passage must be opened by bending the breaking member (106) with hands after sticking the rubber plug (108) of the vial (101) with the needle (105). Moreover, when the bending of the breaking member (106) is incomplete, fluid is hard to pass through the tube so that it takes much time to carry out the dissolution of the drug. In addition, the number of parts is relatively large and this results in high cost.

SUMMARY OF THE INVENTION

The present invention was made to eliminate the above mentioned drawbacks, and is intended to provide a transfusion device which is simple in construction and permits sure and easy communication between a drug container and a vessel of a liquid for dissolving a drug (which liquid is hereinafter referred to as a solvent fluid), and which enables the drug and solvent fluid to be mixed in short time and is low in cost.

According to the present invention there is provided a transfusion device comprising a flexible vessel containing a solvent fluid, a plugged drug container containing a drug, and a communicating portion for communicating the drug container and the flexible vessel with each other, wherein the communicating portion comprises a communicating passage leading to the interior of the flexible vessel integrally through an upper portion thereof and having the drug container fitted partially or wholly into a top portion thereof, the plugged mouth portion of the drug container facing downward, a membrane disposed in the communicating passage for closing the passage, and a puncturing needle unit disposed beneath the membrane and axially slidable along the inner periphery of said communicating passage such that when an external pressing force is applied through the flexible vessel, the needle unit can slide upward to break said membrane and a plug member of the drug container thereby to allow the drug container and the flexible vessel to communicate with each other.

In the device of the invention, the plugged drug container and the flexible vessel are connected together by the communicating portion which is closed by a particular membrane. A puncturing needle unit is axially slidably disposed in the communicating passage such that by pressing the needle unit externally through the flexible vessel in the axial direction or in a direction generally perpendicular to the axis, the needle is caused to break the membrane of the communicating portion and the plug member of the drug container, the two containers being thus caused to internally communicate with each other. Through this procedure, the drug and the solvent fluid are mixed together to provide a transfusion liquid.

In essence, the invention makes it possible to prepare a transfusion liquid in an accurate manner simply by pressing the puncturing needle unit in the flexible vessel externally therethrough. According to the invention, therefore, easy and very positive communication between the two containers can be effected, with an added advantage that fewer parts are required and lower costs are involved.

DETAILED DESCRIPTION OF THE PREFERRED EMBODIMENTS

The invention will now be described in further detail with reference to an embodiment shown in FIG. 1. It is understood, however, that the invention is not limited by the embodiment.

Figure 1:
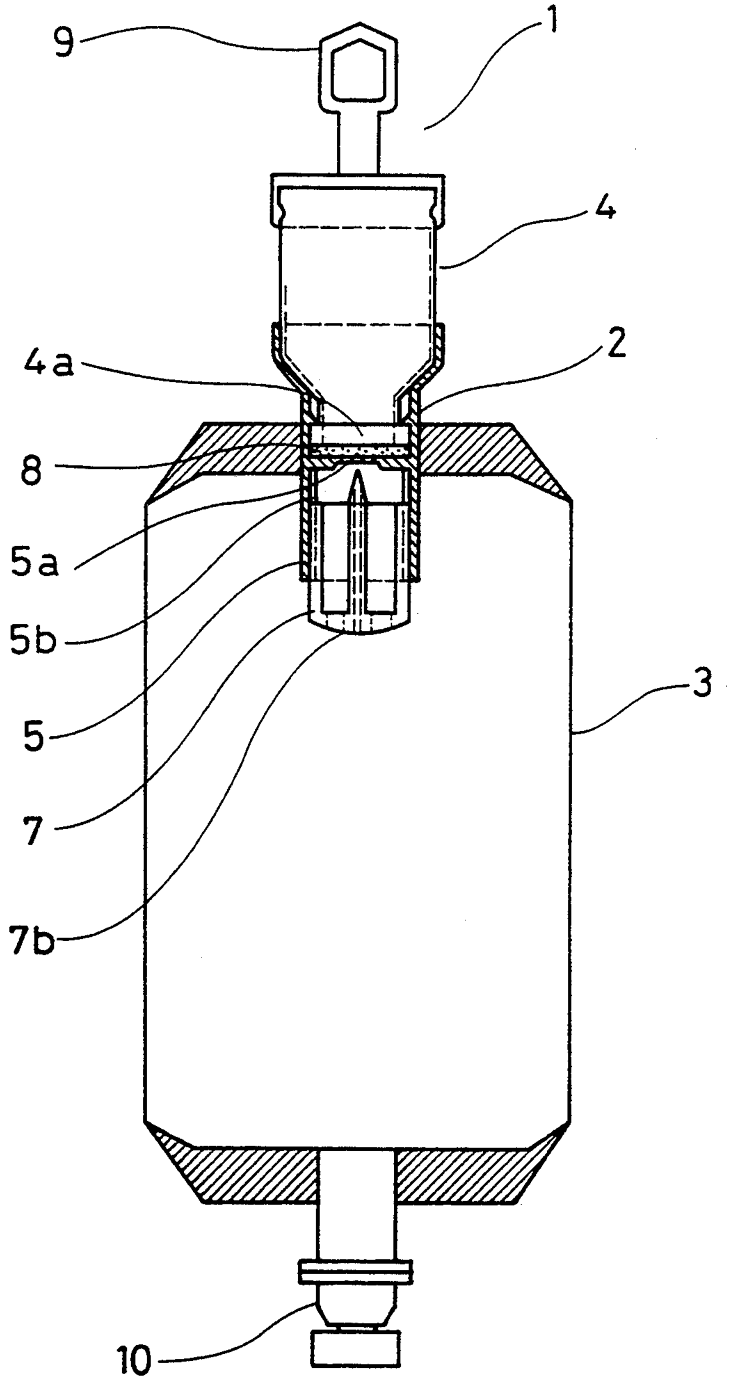
FIG. 1 is an assembly view in section showing one embodiment of the invention.

In FIG. 1, a transfusion device (container) (I) comprises a flexible vessel in the form of a bag (3) which contains therein a solvent fluid in sterilized condition, a drug vial (hereinafter referred to as a vial) (4), as a drug container, which contains therein a solid drug in sterilized condition, and a communicating portion (2) for allowing the vial (4) and the bag (3) to communicate with each other. In FIG. 1 is shown an embodiment in which the vial (4) is partially fitted in a top portion of a communicating passage (5), the plugged mouth portion (4*a*) (i.e., the mouth portion (4*a*) is closed by a plug member not shown) of the vial being shown as facing downward (FIG. 1; where a similar directional expression "upward" or "downward" is referred to in the following description, the directional relationship in FIG. 1 will apply). The reference numeral (9) denotes a suspension member made of a soft polypropylene resin which is provided on the top of the vial (4). The reference numeral (10) denotes a fluid outlet provided in a lower portion of the bag(3).

The bag (3) is made of a flexible material, such as a soft vinyl chloride resin, a polyolefin resin or an ethylene vinyl acetate coplolymer. For use as such a material, a polyolefin resin is preferred because it has good chemical resistance and is little likely to be eluded in the solvent fluid.

Examples of solvents fluid suitable for being contained in the bag (3) include a physiological saline solution, a 5% glucose solution, distilled water for infusion, and also a solution containing various electrolytes.

The vial (4) (container body) is made of glass and contains a solid drug therein, the mouth (4*a*) of the vial being closed by a plug member not shown.

Examples of drugs which may be contained in the vial (4) include antibiotics, antitumer agents, and antiulcer agents.

Examples of antibiotics include cephem antibiotics, such as cefazolin sodium, ceftizoxime sodium, cefotiam dihydrochloride, cefmenoxime hemihydrochloride, cephacetvile sodium, cefamandole sodium, cephalovidine, cefotaxime sodium, cefotetan sodium, cefoperazone sodium, cefsulodin sodium, ceftezole sodium, cefpiramide sodium, cefmetazole sodium, and cefuroxime sodium; and penicillin antibiotics, such as ampicillin sodium, carbenicillin disodium, sulbenicillin disodium, and ticarcillin sodium. Examples of antitumor agents include mitomycin C, fluorouracil, tegafur, and cytarabine. Examples of antiulcer agents include famotidine, ranitidine hydrochloride, and cimetidine.

The communicating portion (2) comprises a communicating passage (5) leading to the interior of the bag (3) through a top portion thereof integrally therewith and having a plugged portion of the vial (4) fitted into a top portion thereof, a membrane (5*a*) disposed in the communicating passage (5) for closing the passage, a disk (8) disposed as a spacer on the membrane (5*a*), and a hollow puncturing needle unit (7) disposed below the membrane (5*a*) and slidable axially along the inner periphery of the communicating passage (5). It is noted that the disk (8) need not be provided depending upon the configuration of the plug member which closes the mouth portion (4*a*) of the vial (4). Assembling of these parts is performed in a sterile room.

Figure 2:
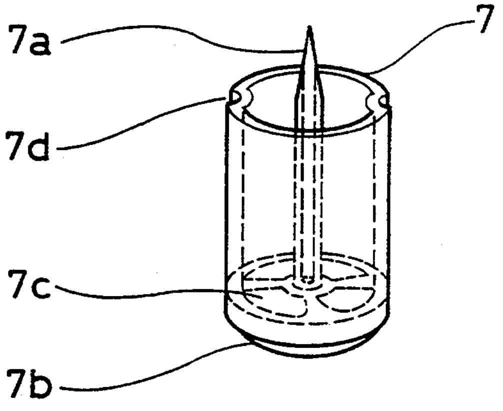
FIG. 2 is a perspective view of a puncturing needle unit as seen in FIG. 1.

The puncturing needle unit (7) has a bottomed cylindrical slider portion and a hollow puncturing needle (7*a*) centrally disposed therein, as shown in FIG. 2. The bottom plate (7*b*) of the slider portion has sectoral slits (7*c*) formed around the puncturing needle (7*a*). The outer diameter of the cylinder is generally the same as the inner diameter of the communicating passage (5), and the cylinder is formed on its outer periphery with vertical grooves (7*d*) adapted to engage vertical ledge-like guides (5*b*) axially formed on the periphery of the communicating passage (5).

Figure 3:
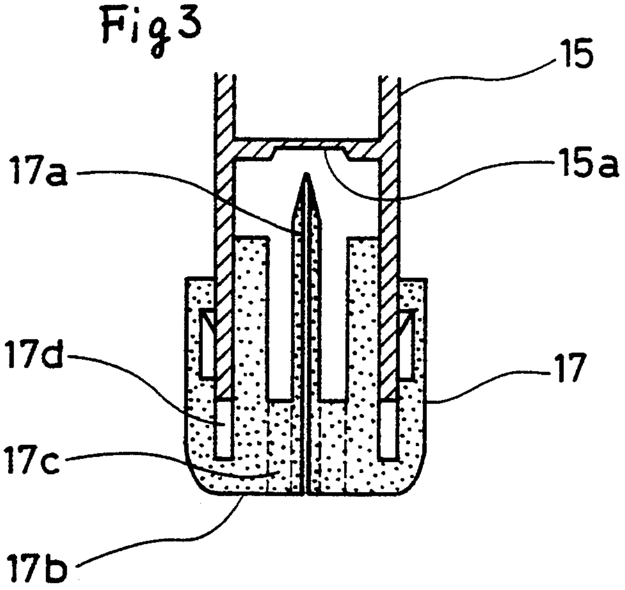
FIG. 3 is a vertical sectional view showing another form of the puncturing needle unit in FIG. 1.

In FIG. 3 is shown another form of puncturing needle unit (17) which is different from the puncturing needle unit (7) shown in FIG. 2, but is equally applicable for use. This needle unit is of a bottomed double cylindrical configuration. Reference numeral (17*a*) designates a hollow puncturing needle, (17*b*) designates a bottom plate, and (17*c*) designates a through-hole. A space (17*d*) is provided for enabling the puncturing needle (17) to slide toward a membrane (15*a*) in the communicating passage (15).

In any case, the puncturing needle unit (7) is preferably made of plastics, because it may come in contact with solvent fluid in the interior of the bag (3).

Nextly, how to use the transfusion device (1) constructed as above described will be explained.

In FIG. 1, the bag (3) is bent at a point slightly below the bottom plate (7*b*) of the puncturing needle unit (7). The bottom plate (7*b*) of the puncturing needle unit (7) is pressed externally through the bag (3). Then, the needle unit (7) slides in the communicating passage (5) toward the membrane (5*a*) and breaks the membrane (5*a*), then breaks the disk (8) and the plug member of the vial (4), so that the interior of the bag (3) and the interior of the vial (4) are enabled to communicate with each other. Then, intermittent compression is applied to the bag (3) to cause the solvent fluid in the bag (3) to move through the hollow puncturing needle (7*a*) to the vial (4) and back therefrom, thereby to dissolve the drug in the vial (4). Thus, a uniform transfusion fluid can be obtained in the transfusion device (1), namely an interconnected assembly of vial (4) and bag (3).

As stated above, the transfusion device (1) has a smaller number of parts and is less expensive, and enables preparation of infusion liquid more easily in short time simply by bending the bag (3) and pressing the puncturing needle unit (7).

Figure 4:
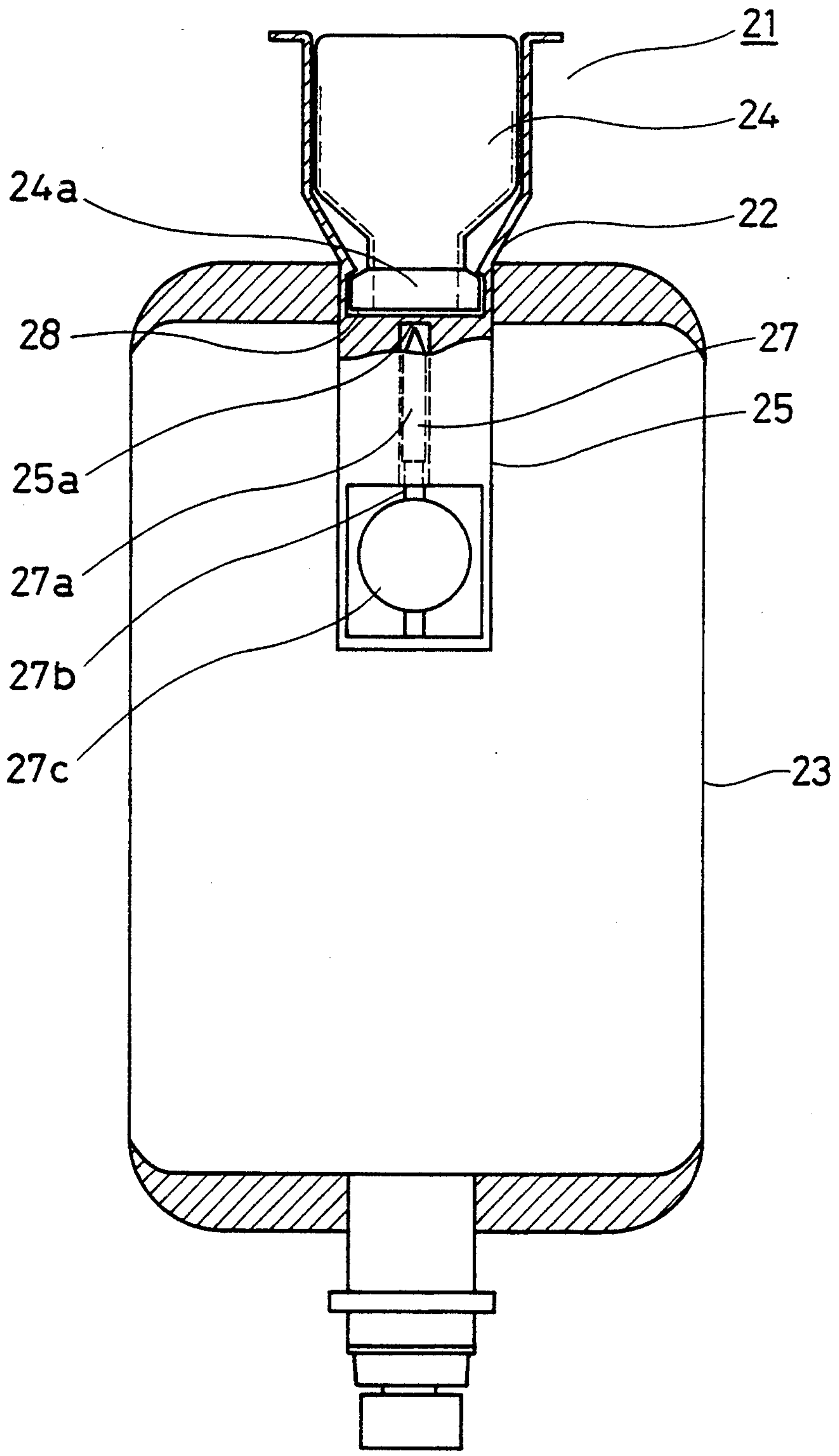
FIG. 4 is an assembly view in section showing another embodiment.

Another embodiment which is different from the foregoing embodiment is shown in FIG. 4. This another embodiment is generally identical with the embodiment shown in FIG. 1, except the arrangement of the puncturing needle unit and communicating passage.

In FIG. 4, reference numeral (21) designates a transfusion device, (22) designates a communicating portion, (23) designates a bag (flexible vessel), (24) designates a plugged vial (drug container), (25) designates a communicating passage, (25*a*) designates a membrane, (27) designates a puncturing needle unit, and (28) designates a disk. In the FIG. 4 embodiment, the vial (24) having its plugged mouth portion (24*a*) (i.e., the mouth portion (24*a*) oriented downward is closed by a plug member not shown) is wholly fitted in the communicating passage (25).

Figure 5:
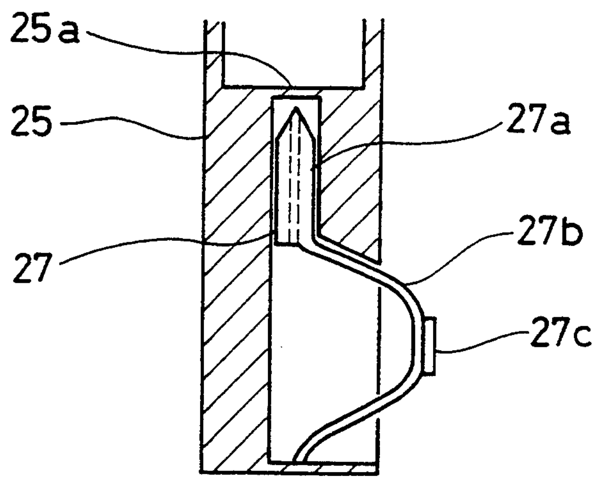
FIG. 5 is a vertical sectional view showing the puncturing needle unit and adjacent parts in FIG. 4.

The puncturing needle unit (27) comprises a hollow needle (27*a*), a resilient material piece (27*b*) serving as a direction changing member, and a pushbutton (27*c*) disposed generally perpendicularly to the axis of the communicating passage (25). The communicating passage (25) is adapted for having a puncturing needle unit (27) mounted therein. In FIG. 5, the needle unit is shown in vertical section as mounted in position.

In use, the pushbutton (27*c*) is depressed externally through the bag (23). Then, the needle (27*a*) slides upward in the communicating passage (25) through the resilient material piece (27*b*) to break the membrane (25*a*), then breaking the disk (28) and the plug member of the vial (24). Thus, the interior of the bag (23) and the interior of the vial (24) are interconnected.

Other forms of puncturing needle unit which are applicable for use in the FIG. 4 embodiment of the transfusion device are shown in vertical section in FIGS. 6 through 10.

Figure 6:
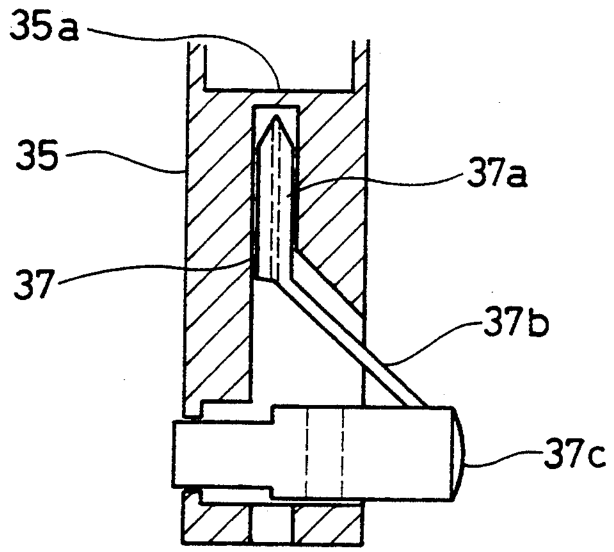
FIG. 6 is a vertical sectional view showing another form of the puncturing needle unit in FIG. 4.
Figure 7:
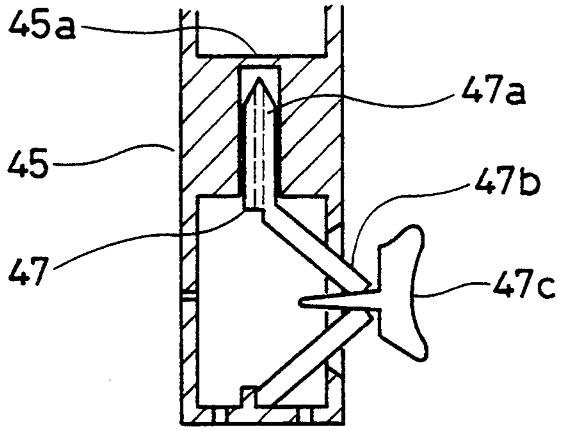
FIG. 7 is a vertical sectional view showing a further form of the puncturing needle unit in FIG. 4.
Figure 8:
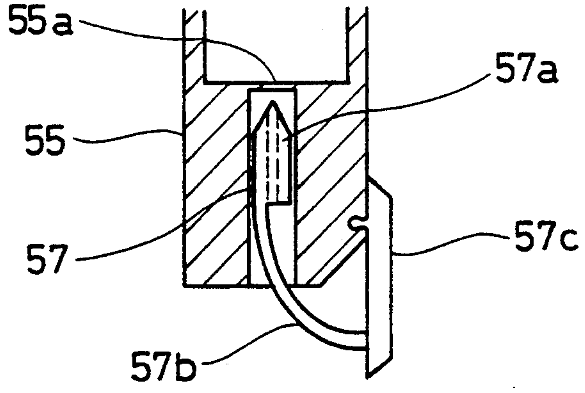
FIG. 8 is a vertical sectional view showing still another form of the puncturing needle unit in FIG. 4.

In FIG. 6, when a pushbutton (37*c*) of a puncturing needle unit (37) is depressed, a hollow needle (37*a*) slides in a communicating passage (35) through a resilient material piece (37*b*). The needle breaks a membrane (35*a*) and then breaks the disk and the plug member of the vial (both not shown). The embodiments shown in FIGS. 7 and 8 are of a similar construction and are similarly effective.

Figure 9:
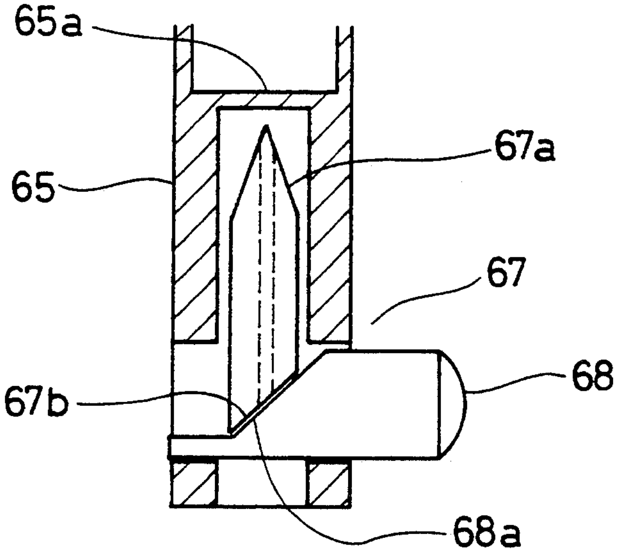
FIG. 9 is a vertical sectional view showing another form of puncturing needle unit different in construction from the one shown in FIG. 4.

The embodiment shown in FIG. 9 represents a puncturing needle unit (67) utilizing slanted members as a direction changing member. The hollow needle (67*a*) and the pushbutton (68) are provided respectively with slanted portions (67*b*), (68*a*) at their rear portions which are held in engagement with each other. When the pushbutton (68) is depressed, the needle (67*a*) slides in the communicating passage (65) under the action of the slanted portions, thus breaking the membrane (65*a*).

Figure 10:
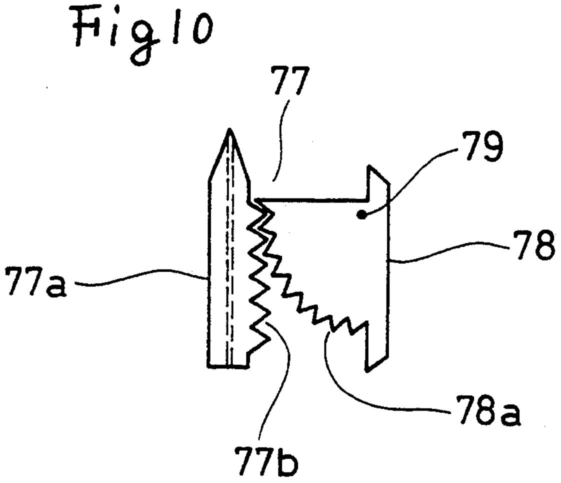
FIG. 10 is a vertical sectional view showing still another form of puncturing needle unit different in construction from the one shown in FIG. 4.
Figure 11:
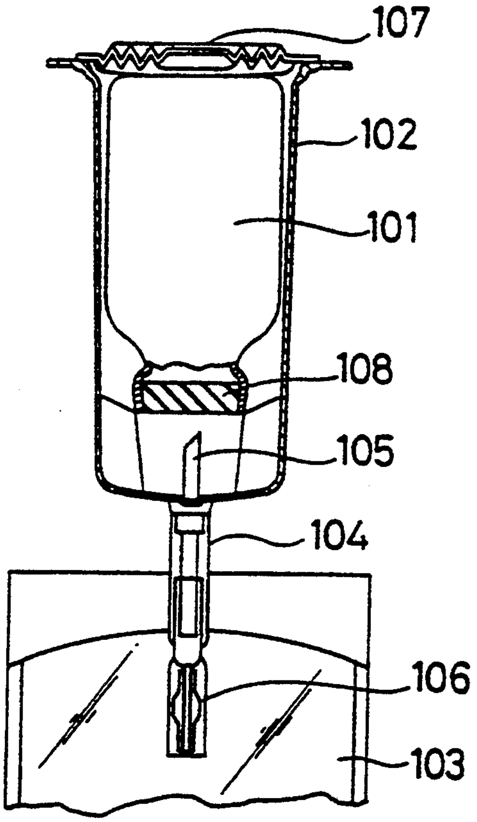
Fig11 PRIOR ART
FIG. 11 is a front view, partly in section, showing a prior art arrangement.

The embodiment shown in FIG. 10 represents a puncturing needle unit (77) utilizing geared members as a direction changing member. A hollow needle (77*a*) is partly provided with a rack portion (77*b*), and a pushbutton (78) is partly provided with a pinion portion (78*a*), the rack and pinion portions being held in mesh engagement. When the pushbutton (78) is depressed, the pinion portion (78*a*) pivots about a pin (79) and the needle (77*a*), under the action of the rack portion (77*b*) in mesh with the pinion portion, slides upward to break the membrane (not shown).

According to the invention, the drug container and the flexible vessel can be brought into communication with each other simply by pressing the puncturing needle unit externally through the flexible vessel. Therefore, easy and very positive communication between containers can be achieved and, in addition, fewer parts are required and costs involved are lower, as compared with any conventional transfusion device.

What is claimed is:

1. A transfusion device comprising a flexible vessel containing a solvent fluid, a drug container containing a drug, and a communicating portion for communicating the drug container and the flexible vessel with each other;

wherein the communicating portion comprises a communicating passage leading to the interior of the flexible vessel integrally through an upper portion thereof and having the drug container fitted partially or wholly into a top portion thereof, said drug container including a mouth with a plug member therein to form a plugged mouth portion, the plugged mouth portion of the drug container facing downward, a membrane disposed in the communicating passage for closing the communicating passage, and a slidably mounted puncturing needle unit disposed beneath the membrane and axially slidable along an inner periphery of said communicating passage such that when an external pressing force is applied through the flexible vessel the slidably mounted puncturing needle unit slides upward with respect to said inner periphery of said communicating passage and with respect to said flexible vessel to break said membrane and to penetrate the plug member of the drug container thereby to allow the drug container and the flexible vessel to communicate with each other.

2. A transfusion device as set forth in claim 1, wherein the puncturing needle unit has a slider portion axially slidable within the communicating passage, and a hollow puncturing needle disposed upright in the slider portion, so that when the bottom of the slider portion is pressed axially upward through the flexible vessel, the needle can be moved axially upwardly to break the membrane and the plug member of the drug container thereby to allow the drug container and the flexible vessel to communicate with each other.

3. A transfusion device comprising:

a flexible vessel containing a solvent, a drug container containing a drug, and a communicating portion for communicating the drug container and the flexible vessel with each other;

said communicating portion including a communicating passage extending into the interior of the flexible vessel through an upper portion thereof, said drug container connected to a top portion of said communicating portion with said drug container facing downward, a membrane disposed in the communicating passage for closing the communicating passage, and a puncturing needle unit disposed beneath the membrane and axially slidable along an inner periphery of said communicating passage such that when an external pressing force is applied through the flexible vessel, the needle unit slides upward to break said membrane to allow the drug container and the flexible vessel to communicate with each other; and wherein the puncturing needle unit comprises a hollow puncturing needle, a pushbutton, and a direction changing member interposed between the needle and the pushbutton, so that when said pushbutton is depressed in a direction generally perpendicular to an axis of the communicating passage, said puncturing needle can be moved axially upward through said direction changing member to break the membrane to allow the drug container and the flexible vessel to communicate with each other.

4. A transfusion device comprising:

a vessel containing a solvent fluid, a container containing a drug, and a communicating portion for communicating the drug container and the vessel with each other;

said communicating portion including a first section receiving at least part of said container, said communicating portion further including a second section at least partially extending into an interior of said vessel, said container including a mouth having a plug member therein to form a plugged mouth portion, said plugged mouth portion of said container disposed in said first section of said communicating portion;

a puncturing needle unit slidably disposed in said second section of said communicating portion, said puncturing needle unit including a puncturing member, said puncturing needle unit slidably disposed within said second section of said communicating portion to be movable along a path said path including a first position at which said puncturing member is spaced from said plugged mouth portion of said container, said path further including a second position at which said puncturing member extends through said plug member of said plugged mouthed portion; and a membrane disposed in said communicating portion at an interface between said first and second sections of said communicating portion, and wherein when said needle unit is in said first position said puncturing member is spaced from said membrane with said membrane disposed between said puncturing member and said plug member, and wherein when said needle unit is in said second position said puncturing member extends through said membrane.

5. The transfusion device of claim 4, wherein said puncturing needle unit further includes a pushbutton movable in a direction perpendicular to said path of said needle unit, said puncturing needle unit further including direction changing means interposed between said puncturing member and said pushbutton for transmitting movement of said pushbutton therethrough and causing movement of said puncturing member along said path in response to movement of said pushbutton.

* * * * *